(12) United States Patent
Brotherton-Pleiss et al.

(10) Patent No.: US 9,359,337 B2
(45) Date of Patent: Jun. 7, 2016

(54) ACETAMIDE DERIVATIVES

(71) Applicant: Hoffmann-La Roche Inc., Little Falls, NJ (US)

(72) Inventors: Christine E. Brotherton-Pleiss, Sunnyvale, CA (US); Zhi Chen, Livingston, NJ (US); Shawn David Erickson, Leonia, NJ (US); Yimin Qian, Plainsboro, NJ (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/712,655

(22) Filed: May 14, 2015

(65) Prior Publication Data

US 2015/0246906 A1    Sep. 3, 2015

Related U.S. Application Data

(63) Continuation of application No. PCT/EP2013/073521, filed on Nov. 11, 2013.

(60) Provisional application No. 61/726,154, filed on Nov. 14, 2012.

(51) Int. Cl.
| | | |
|---|---|---|
| *C07D 211/26* | (2006.01) | |
| *C07D 413/04* | (2006.01) | |
| *C07D 265/30* | (2006.01) | |
| *C07D 207/09* | (2006.01) | |

(52) U.S. Cl.
CPC .......... *C07D 413/04* (2013.01); *C07D 207/09* (2013.01); *C07D 211/26* (2013.01); *C07D 265/30* (2013.01)

(58) Field of Classification Search
CPC ... C07D 401/12; C07D 211/26; C07D 213/59
USPC ................. 514/235.5, 331; 544/131; 546/234
See application file for complete search history.

(56) References Cited

FOREIGN PATENT DOCUMENTS

| WO | 00/49007 A1 | 8/2000 |
|---|---|---|
| WO | WO 2010/141805 | * 12/2010 |

OTHER PUBLICATIONS

Bautista et al Annu. Rev. Physiol. 2013, 75, 181-200.*
International Preliminary Report on Patentability issued in International Application No. PCT/EP2013/073521, dated May 19, 2015, in 6 pages.
International Search Report issued in International Application No. PCT/EP2013/073521, dated Dec. 13, 2013, in 4 pages.

* cited by examiner

*Primary Examiner* — Celia Chang
(74) *Attorney, Agent, or Firm* — Lily J. Ackerman

(57) ABSTRACT

The invention is concerned with a compound of formula (I)

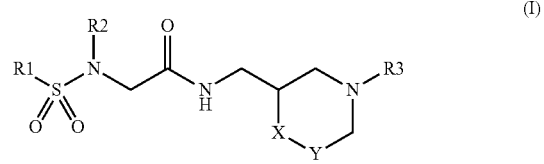

and pharmaceutically acceptable salts thereof wherein R1 to R3, X and Y are as defined as in the description and in the claims. The compound of formula (I) can be used as a medicament.

18 Claims, No Drawings

ACETAMIDE DERIVATIVES

This application is a continuation of International Application No. PCT/EP2013/073521 having an international filing date of Nov. 11, 2013, the entire contents of which are incorporated herein by reference, and which claims benefit under 35 U.S.C. §119 to U.S. Provisional Patent Application No. 61/726,154 filed Nov. 14, 2012, the entire contents of which are incorporated herein by reference.

The present invention relates to organic compounds useful for therapy and/or prophylaxis in a mammal of an inflammatory disease or disorder, and in particular to Transient Receptor Potential (TRP) channel antagonists, their manufacture and pharmaceutical compositions containing them.

The invention relates in particular to a compound of formula (I)

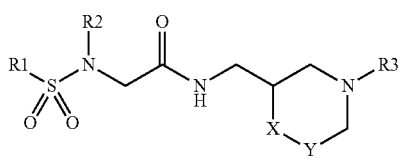

wherein:
X is —CH$_2$— or oxygen;
Y is —(CH$_2$)$_n$—;
R1 is phenyl optionally substituted with halogen;
R2 is lower alkyl;
R3 is trifluoromethyl-phenyl, trifluoromethyl-pyridinyl, trifluoromethyl-pyridazinyl, trifluoromethyl-pyrimidinyl or trifluoromethyl-pyrazinyl; and
n is 0 or 1, provided that n is not 0 when X is oxygen;
or a pharmaceutically acceptable salt thereof.

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor'. Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation.

The invention also provides for pharmaceutical compositions comprising the compounds, methods of using the compounds and methods of preparing the compounds.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1 to R3 of formula (I) refer to moieties that are attached to the core structure of formula (I) by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl. Particular examples of lower alkyl are methyl, ethyl and isopropyl.

The terms "halo", "halogen" and "halide", which may be used interchangeably, refer to a substituent fluoro, chloro, bromo, or iodo. Fluoro is a particular example of halogen.

Unless otherwise indicated, the term "hydrogen" or "hydro" refers to the moiety of a hydrogen atom (—H) and not H$_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula (I) to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula (I) (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The invention relates in particular to:

A compound of formula (I) wherein X is —CH$_2$—;

A compound of formula (I) wherein X is oxygen;

A compound of formula (I) wherein n is 0;

A compound of formula (I) wherein n is 1;

A compound of formula (I) wherein R1 is halophenyl;

A compound of formula (I) wherein R1 is fluoro-phenyl;

A compound of formula (I) wherein R2 is methyl, ethyl, isopropyl or tert-butyl;

A compound of formula (I) wherein R2 is methyl, ethyl or isopropyl;

A compound of formula (I) wherein R3 is trifluoromethyl-phenyl or trifluoromethyl-pyridinyl;

A compound of formula (I) wherein, wherein R3 is trifluoromethyl-phenyl or trifluoromethyl-pyridinyl;

A compound of formula (I) wherein, wherein R3 is trifluoromethyl-phenyl; and

A compound of formula (I) wherein R3 is trifluoromethyl-pyridinyl.

The invention further relates in particular to a compound of formula (I) selected from:

2-[Ethyl-(4-fluoro-benzenesulfonyl)-amino]-N-[1-(4-trifluoromethyl-phenyl)-piperidin-3-ylmethyl]-acetamide;
2-[(4-Fluoro-benzenesulfonyl)-isopropyl-amino]-N-[1-(4-trifluoromethyl-phenyl)-piperidin-3-ylmethyl]-acetamide;
2-[Ethyl-(4-fluoro-benzenesulfonyl)-amino]-N-[1-(4-trifluoromethyl-phenyl)-pyrrolidin-3-ylmethyl]-acetamide;
2-[(4-Fluoro-benzenesulfonyl)-isopropyl-amino]-N-[1-(4-trifluoromethyl-phenyl)-pyrrolidin-3-ylmethyl]-acetamide;
2-[(4-Fluoro-benzenesulfonyl)-isopropyl-amino]-N—[(S)-1-(4-trifluoromethyl-phenyl)-piperidin-3-ylmethyl]-acetamide;
2-[(4-Fluoro-benzenesulfonyl)-isopropyl-amino]-N—[(R)-1-(4-trifluoromethyl-phenyl)-piperidin-3-ylmethyl]-acetamide;
2-[(4-Fluoro-benzenesulfonyl)-methyl-amino]-N-[4-(4-trifluoromethyl-phenyl)-morpholin-2-ylmethyl]-acetamide;
2-[(4-Fluoro-benzenesulfonyl)-isopropyl-amino]-N-[4-(4-trifluoromethyl-phenyl)-morpholin-2-ylmethyl]-acetamide;
2-[Ethyl-(4-fluoro-benzenesulfonyl)-amino]-N-[4-(4-trifluoromethyl-phenyl)-morpholin-2-ylmethyl]-acetamide;
2-[(4-Fluoro-benzenesulfonyl)-isopropyl-amino]-N—[(R)-4-(4-trifluoromethyl-phenyl)-morpholin-2-ylmethyl]-acetamide;
2-[(4-Fluoro-benzenesulfonyl)-isopropyl-amino]-N—[(S)-4-(4-trifluoromethyl-phenyl)-morpholin-2-ylmethyl]-acetamide; and
2-[(4-Fluoro-benzenesulfonyl)-isopropyl-amino]-N-[4-(5-trifluoromethyl-pyridin-2-yl)-morpholin-2-ylmethyl]-acetamide.

The invention also relates to:

A pharmaceutical composition, comprising a therapeutically effective amount of a compound according to formula (I) and a pharmaceutically acceptable carrier;

A compound according to formula (I) for use as a therapeutically active substance;

The use of a compound of formula (I) for the treatment or prophylaxis of a respiratory disorder;

The use of a compound according to formula (I) for the preparation of a medicament for the treatment or prophylaxis of a respiratory disorder;

A compound according to formula (I) for use in the treatment or prophylaxis of a respiratory disorder; and A method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

Examples of respiratory disorder are chronic obstructive pulmonary disorder (COPD), asthma, allergic rhinitis or bronchospasm.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in Scheme 1.

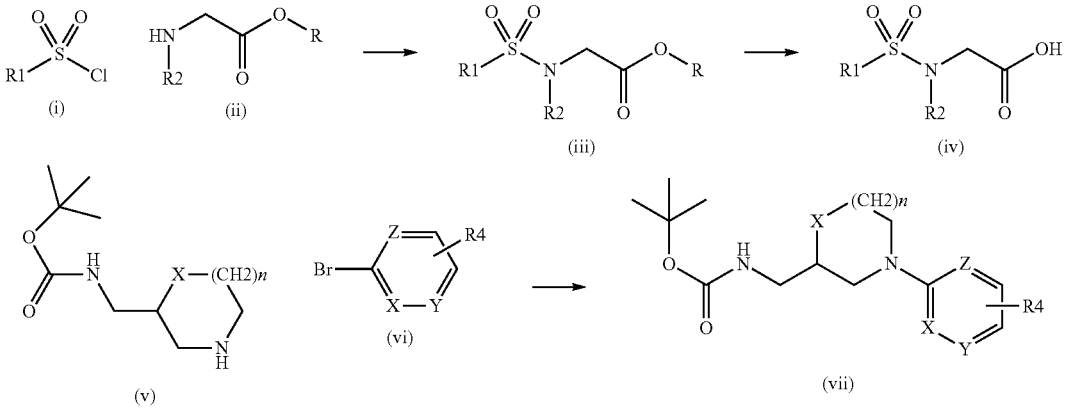

-continued

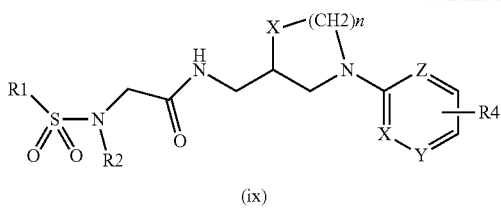

(ix)

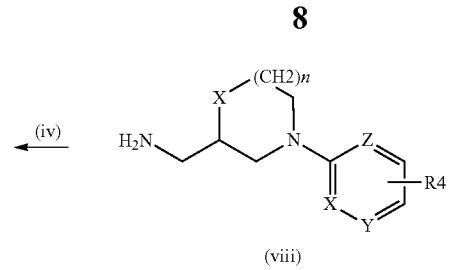

(viii)

As described in Scheme 1, the N-substituted glycine ester (ii) can react with sulfonyl chloride (i) in the presence of base, such as triethylamine, to form the intermediate sulfonamide (iii), where R can be methyl or ethyl groups, R1 can be aryl, heteroaryl and aryl substituted with halogens, and R2 can be lower alkyl groups, such as methyl, ethyl or isopropyl groups. The hydrolysis of ester (iii) under mild conditions, such as aqueous lithium hydroxide solution in THF, can provide the desired intermediate carboxylic acid (iv).

The coupling reaction between the cyclic amine (v) and the arylbromide (vi) under palladium catalysis conditions can provide the N-aryl intermediate (vii). R4 is trifluoromethyl. The general Buchwald amination reaction conditions can be used to accomplish the N-arylation reaction. The detailed description can be found in the preparation procedure of the corresponding intermediates. For compound (v), the n number can be 0 or 1 (five or six membered cyclic amine). When the number n is 0, the X is ($CH_2$). When the number n is 1, the X can be ($CH_2$) or oxygen. For compound (vi), X, Y and Z can be (CH) or N. The cleavage of the butoxycarbonyl group in (vii) can give the corresponding primary amine (viii), which can be stored either as the free amine or the hydrochloride salt.

Finally, the coupling between the carboxylic acid (iv) and the amine (viii) in the presence of coupling reagents can afford the desired compound (ix). The coupling reagents used in peptide chemistry for amide formation can be used. The detailed conditions can be found in the examples.

The invention thus also relates to a process for the manufacture of a compound of formula (I) comprising the reaction of a compound of formula (A)

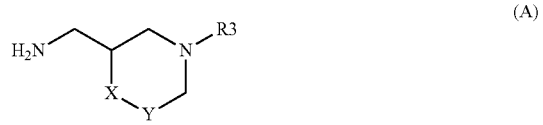
(A)

in the presence of a compound of formula (B)

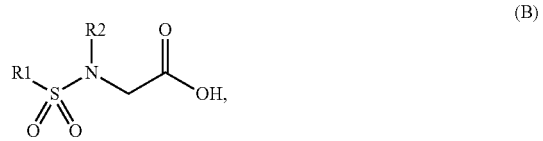
(B)

a coupling agent and a base, wherein R1 to R3 are as defined above.

Examples of coupling agents useful in the process of the invention are known amide formation coupling agents, like for example HATU.

Diisopropylethylamine is an example of suitable base for the above process.

The invention thus also relates to a compound of formula (I) when manufactured by the process of the invention.

The invention will now be illustrated by the following examples which have no limiting character.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 µm, 20×150 mm) from Varian, Inc., an Xbridge™ Prep $C_{18}$ column (5 µm, OBD™ 20×100 mm) from Waters Corporation, or a SunFire™ Prep $C_{18}$ column (5 µm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex® II FTICR with a 4.7 Tesla magnet (from Bruker Corporation), a Waters® Alliance® 2795-ZQ™2000 (from Waters Corporation), or an MDS Sciex™ API-2000™ n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.

Absolute stereochemistry, where assigned, is based on comparison of biological potency and/or relative retention time on silica gel TLC and chromatography to analogs prepared from chiral building blocks of known absolute configuration.

INTERMEDIATES

[(4-Fluoro-benzenesulfonyl)-methyl-amino]acetic acid

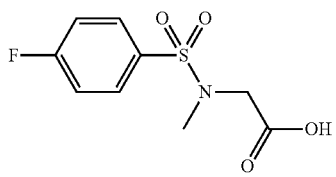 [SMILES: CN(CC(=O)O)S(=O)(=O)c1ccc(F)cc1]

4-Fluorobenzene-1-sulfonyl chloride (1.95 g, 10 mmol) and ethyl 2-(methylamino)acetate hydrochloride (1.54 g, 10 mmol) were suspended in dichloromethane (50 mL). Under ice bath, triethylamine (4.2 mL) was added and the mixture was stirred at room temperature for 4 h. Solvents were evaporated and the residue was treated with ethyl acetate (60 mL), extracted with water, sodium bicarbonate solution and finally diluted hydrochloric acid solution. The organic layer was washed with water and dried. Solvents were evaporated and the residue was dried in vacuo to give an oily material (2.27 g) as [(4-fluoro-benzenesulfonyl)-methyl-amino]-acetic acid ethyl ester.

Ethyl 2-(4-fluoro-N-methylphenylsulfonamido)acetate (2.27 g) was dissolved in THF (20 mL) and 0.5 N LiOH solution (20 mL) was added. The mixture was stirred at room temperature for 5 h. Solvents were evaporated and the residue was dissolved in water, filtered and acidified with hydrochloric acid. The white solid was filtered to give [(4-fluoro-benzenesulfonyl)-methyl-amino]-acetic acid (1.68 g). LRMS calcd for $C_9H_{10}FNO_4S$ (m/e) 247.0; obsd 246.1 (ES$^-$).

[Ethyl-(4-fluoro-benzenesulfonyl)-amino]-acetic acid

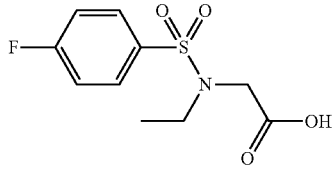 [SMILES: CCN(CC(=O)O)S(=O)(=O)c1ccc(F)cc1]

This intermediate was prepared using the same procedure described for the preparation of [(4-fluoro-benzenesulfonyl)-methyl-amino]-acetic acid. LRMS calcd for $C_{10}H_2FNO_4S$ (m/e) 261.0; obsd 260.1 (ES$^-$).

[(4-Fluoro-benzenesulfonyl)-isopropyl-amino]acetic acid

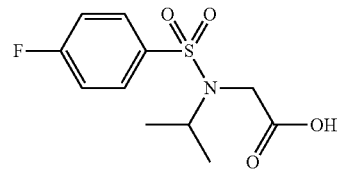 [SMILES: CC(C)N(CC(=O)O)S(=O)(=O)c1ccc(F)cc1]

This intermediate was prepared using the same procedure described for the preparation of [(4-fluoro-benzenesulfonyl)-methyl-amino]-acetic acid. LRMS calcd for $C_{11}H_4FNO_4S$ (m/e) 275.0; obsd 274.1 (ES$^-$).

[1-(4-Trifluoromethyl-phenyl)-piperidin-3-ylmethyl]-carbamic acid tert-butyl ester

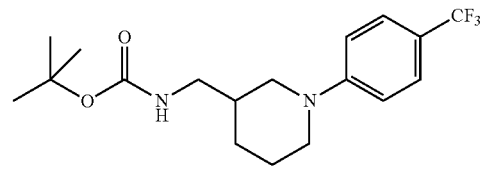 [SMILES: CC(C)(C)OC(=O)NCC1CCCN(c2ccc(C(F)(F)F)cc2)C1]

A solution of piperidin-3-ylmethyl-carbamic acid tert-butyl ester (1.00 g, 4.67 mmol), 1-bromo-4-trifluoromethyl-benzene (1.15 g, 5.13 mmol), sodium tert-butoxide (673 mg, 7.00 mmol), (R)-(+)-2,2'-bis(diphenylphosphino)-1,1'-binaphthyl (291 mg, 0.47 mmol) and tris(dibenzylideneacetone)-dipalladium (0) (214 mg, 0.23 mmol) in toluene (5 mL) at 25° C. was purged with nitrogen gas and evacuated three times. The solution was sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Filtration followed by concentration in vacuo to afford crude [1-(4-trifluoromethyl-phenyl)-piperidin-3-ylmethyl]-carbamic acid tert-butyl ester (1.5 g, 90% crude) as a light oil.

[1-(4-Trifluoromethyl-phenyl)-piperidin-3-yl]methylamine

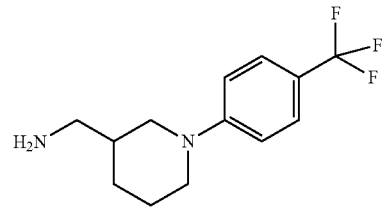 [SMILES: NCC1CCCN(c2ccc(C(F)(F)F)cc2)C1]

A solution of [1-(4-trifluoromethyl-phenyl)-piperidin-3-ylmethyl]-carbamic acid tert-butyl ester (500 mg, 1.4 mmol crude) in ethyl acetate (5 mL) at 25° C. was treated with 1 M hydrogen chloride aqueous solution (1 mL). The reaction mixture was heated to 50° C. for 2 h. The reaction mixture was then cooled to 25° C., poured into water and extracted with ethyl acetate. The aqueous layer was adjusted with ammonium hydroxide aqueous solution to pH about 9-10 and extracted three times with ethyl acetate. The combined organic layers were then dried over magnesium sulfate, filtered and concentrated in vacuo to afford crude [1-(4-trifluoromethyl-phenyl)-piperidin-3-yl]-methylamine (100 mg, 28%, crude) as an oil. [MH]+=259.0.

[1-(4-Trifluoromethyl-phenyl)-pyrrolidin-3-ylmethyl]-carbamic acid tert-butyl ester

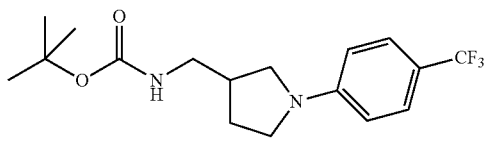 [SMILES: CC(C)(C)OC(=O)NCC1CCN(c2ccc(C(F)(F)F)cc2)C1]

A solution of pyrrolidin-3-ylmethyl-carbamic acid tert-butyl ester (0.50 g, 2.50 mmol), 1-bromo-4-trifluoromethylbenzene (0.62 g, 2.75 mmol), sodium tert-butoxide (0.36 g, 3.47 mmol), (R)-(+)-2,2'-bis(diphenylphosphino)-1,1'-binaphthyl (155 mg, 0.25 mmol) and tris(dibenzylideneacetone)-dipalladium (0) (114 mg, 0.13 mmol) in toluene (5 mL) at 25° C. was purged with nitrogen gas and evacuated three times. The solution was sealed and heated to 120° C. for 14 h. The reaction mixture was cooled to 25° C., unsealed and poured into water. The aqueous phase was extracted three times with ethyl acetate. The combined organic layers were washed with brine and dried over magnesium sulfate. Solvents were evaporated and the residue was purified by flash column chromatography (80/20 hexanes/ethyl acetate) to afford [1-(4-trifluoromethyl-phenyl)-pyrrolidin-3-ylmethyl]-carbamic acid tert-butyl ester (500 mg, 58%) as a light oil.

[1-(4-Trifluoromethyl-phenyl)-pyrrolidin-3-yl]methylamine

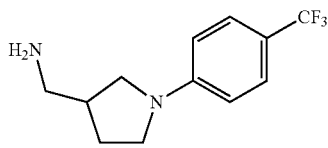 [SMILES: NCC1CCN(c2ccc(C(F)(F)F)cc2)C1]

A solution of [1-(4-trifluoromethyl-phenyl)-pyrrolidin-3-ylmethyl]-carbamic acid tert-butyl ester (500 mg, 1.45 mmol) in ethyl acetate (5 mL) at 25° C. was treated with 1 M hydrogen chloride aqueous solution (1 mL). The reaction mixture was heated to 50° C. for 2 h. The reaction mixture was then poured into water and extracted with ethyl acetate. The aqueous layer was adjusted with 1 M sodium hydroxide solution to pH around 9-10. The aqueous phase was extracted three times with ethyl acetate. The organic layer was then dried over magnesium sulfate, filtered and concentrated in vacuo to afford crude [1-(4-trifluoromethyl-phenyl)-pyrrolidin-3-yl]-methylamine (100 mg, 28%, crude) as an oil. [MH]+=245.0.

[4-(4-Trifluoromethyl-phenyl)-morpholin-2-ylmethyl]-carbamic acid tert-butyl ester

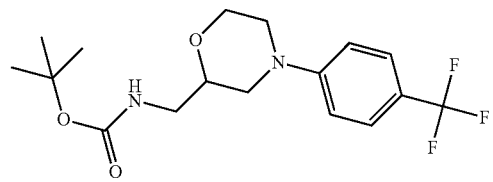 [SMILES: CC(C)(C)OC(=O)NCC1CN(c2ccc(C(F)(F)F)cc2)CCO1]

tert-Butyl morpholin-2-ylmethylcarbamate (1.0 g, 4.62 mmol), 1-bromo-4-(trifluoromethyl)benzene (1.04 g, 4.62 mmol), Pd(dba)$_2$ (133 mg, 0.23 mmol), X-Phos (220 mg, 0.46 mmol) and sodium tert-butoxide (533 mg, 5.55 mol) were combined in 10 mL of dry toluene in a sealed tube. The mixture was degassed with argon and then stirred at 105° C. for 4 h. The mixture was filtered through a layer of Celite and rinsed with THF. Solvents were evaporated and the residue was extracted with water and ethyl acetate. The organic layer was dried and concentrated. The residue was purified by ISCO flash column chromatography (50 g silica gel, ethyl acetate in hexanes 0% to 80%) to give the desired compound (727 mg, 44%).

[4-(4-Trifluoromethyl-phenyl)-morpholin-2-yl]methylamine hydrochloride

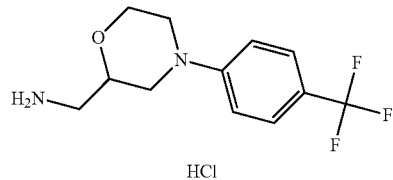 [SMILES: NCC1CN(c2ccc(C(F)(F)F)cc2)CCO1 ; Cl]

tert-Butyl (4-(4-(trifluoromethyl)phenyl)morpholin-2-yl)methylcarbamate (720 mg) was dissolved in dichloromethane (4 mL) and TFA (3 mL) was added. The mixture was stirred at room temperature for 1 h and solvents were evaporated. The residue was treated with dichloromethane and toluene. Solvents were evaporated. The residue was dissolved in dichloromethane (10 mL) and 1N hydrogen chloride in ether was added (10 mL). Solvents were evaporated and the residue was triturated with dry ether and filtered to give the desired hydrochloride salt (485 mg, 82%). [MH]+= 261.

[4-(5-Trifluoromethyl-pyridin-2-yl)-morpholin-2-ylmethyl]-carbamic acid tert-butyl ester

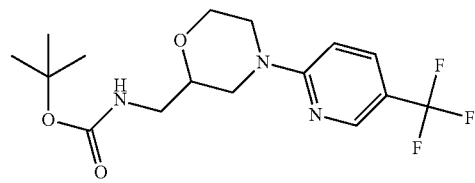 [SMILES: CC(C)(C)OC(=O)NCC1CN(c2ccc(C(F)(F)F)cn2)CCO1]

tert-Butyl morpholin-2-ylmethylcarbamate (1.0 g, 4.62 mmol), 2-chloro-5-(trifluoromethyl)pyridine (839 mg, 4.62 mmol), Pd(dba)$_2$ (133 mg, 0.23 mmol), sodium tert-butoxide (533 mg, 5.55 mmol) and X-Phos (220 mg, 0.46 mmol) were combined in toluene (10 mL). The mixture was degassed with nitrogen for 5 minutes and sealed. The resulting mixture was stirred at 100° C. for 12 h. The mixture was filtered and rinsed with THF. Solvents were evaporated and the residue was purified by ISCO flash column chromatography (0% to 35% ethyl acetate in hexanes) to give the desired compound as a light brown waxy material (350 mg, 21%). [MH]$^+$=362.1.

[4-(5-Trifluoromethyl-pyridin-2-yl)-morpholin-2-yl] methylamine hydrochloride

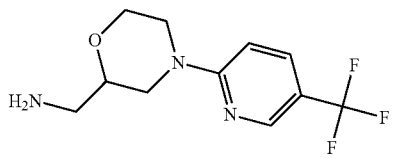 [SMILES: NCC1CN(c2ccc(C(F)(F)F)cn2)CCO1]

tert-Butyl(4-(5-(trifluoromethyl)pyridin-2-yl)morpholin-2-yl)methylcarbamate (350 mg) was dissolved in 3 mL of dichloromethane and 1.5 mL of TFA was added. The mixture was stirred at room temperature for 1 h. Solvents were evaporated and the residue was dried. The residue was re-dissolved in dichloromethane and 1N hydrochloric acid in ether (6 mL) was added. The mixture was concentrated and dried. The residue was suspended in dry ether and the top layer was decanted. The solid material was dried in vacuo to give the desired hydrochloride salt (312 mg, 97%). [MH]$^+$=262.1.

Example 1

2-[Ethyl-(4-fluoro-benzenesulfonyl)-amino]-N-[1-(4-trifluoromethyl-phenyl)-piperidin-3-ylmethyl]-acetamide

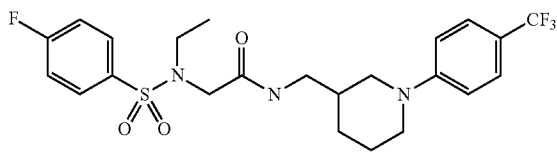 [SMILES: CCN(CC(=O)NCC1CCCN(c2ccc(C(F)(F)F)cc2)C1)S(=O)(=O)c1ccc(F)cc1]

A solution of crude [1-(4-trifluoromethyl-phenyl)-piperidin-3-yl]-methylamine (30.0 mg, 0.12 mmol, crude) and [ethyl-(4-fluoro-benzenesulfonyl)-amino]-acetic acid (30.0 mg, 0.12 mmol) in dichloromethane (5 mL) at 25° C. was treated with HATU (43.7 mg, 0.12 mmol). N,N-Diisopropylethylamine (29.7 mg, 0.23 mmol) was added to the solution. The reaction mixture was stirred for 2 h. The reaction mixture was then poured into 0.2 M aqueous KHSO$_4$ solution and extracted three times with ethyl acetate. The combined organic layers were washed three times with water and once with brine. The organic layer was then dried over magnesium sulfate, filtered and concentrated in vacuo. Flash column chromatography (50/50 hexanes/ethyl acetate) afforded 2-[ethyl-(4-fluoro-benzenesulfonyl)-amino]-N-[1-(4-trifluoromethyl-phenyl)-piperidin-3-ylmethyl]-acetamide (10.2 mg, 18%) as a white solid. [MH]$^+$=502.0.

Example 2

2-[(4-Fluoro-benzenesulfonyl)-isopropyl-amino]-N-[1-(4-trifluoromethyl-phenyl)-piperidin-3-ylmethyl]-acetamide

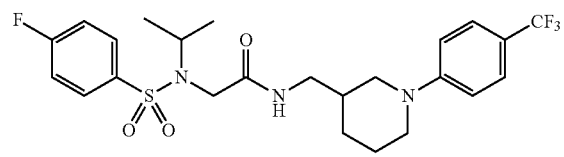 [SMILES: CC(C)N(CC(=O)NCC1CCCN(c2ccc(C(F)(F)F)cc2)C1)S(=O)(=O)c1ccc(F)cc1]

A solution of crude [1-(4-trifluoromethyl-phenyl)-piperidin-3-yl]-methylamine (47.0 mg, 0.18 mmol, crude) and [(4-fluoro-benzenesulfonyl)-isopropyl-amino]-acetic acid (50.0 mg, 0.18 mmol) in dichloromethane (5 mL) at 25° C. was treated with HATU (69.1 mg, 0.18 mmol). N,N-Diisopropylethylamine (46.9 mg, 0.36 mmol) was added to the solution. The reaction mixture was stirred for 2 h. The reaction mixture was then poured into 0.2 M aqueous KHSO$_4$ and extracted three times with ethyl acetate. The combined organic layers were washed three times with water and once with brine. The organic layer was then dried over magnesium sulfate, filtered and concentrated in vacuo. Flash column chromatography (50/50 hexanes/ethyl acetate) afforded 2-[(4-fluoro-benzenesulfonyl)-isopropyl-amino]-N-[1-(4-trifluoromethyl-phenyl)-piperidin-3-ylmethyl]-acetamide (50.0 mg, 53%) as a white solid. [MH]$^+$=516.2.

Example 3

2-[Ethyl-(4-fluoro-benzenesulfonyl)-amino]-N-[1-(4-trifluoromethyl-phenyl)-pyrrolidin-3-ylmethyl]-acetamide

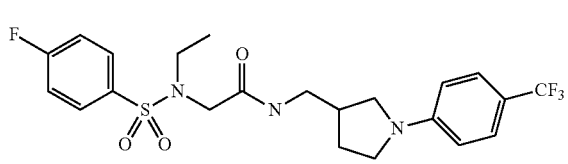 [SMILES: CCN(CC(=O)NCC1CCN(c2ccc(C(F)(F)F)cc2)C1)S(=O)(=O)c1ccc(F)cc1]

A solution of crude [1-(4-trifluoromethyl-phenyl)-pyrrolidin-3-yl]-methylamine (28.0 mg, 0.12 mmol, crude) and [ethyl-(4-fluoro-benzenesulfonyl)-amino]-acetic acid (30.0 mg, 0.12 mmol) in dichloromethane (5 mL) at 25° C. was treated with HATU (43.7 mg, 0.12 mmol). N,N-Diisopropylethylamine (29.7 mg, 0.23 mmol) was added to the solution. The reaction mixture was stirred for 2 h. The reaction mixture was then poured into 0.2 M aqueous KHSO$_4$ and extracted three times with ethyl acetate. The combined organic layers were washed three times with water and once with brine. The organic layer was then dried over magnesium sulfate, filtered and concentrated in vacuo. Flash column chromatography (50/50 hexanes/ethyl acetate) afforded 2-[ethyl-(4-fluorobenzenesulfonyl)-amino]-N-[1-(4-trifluoromethyl-phenyl)-pyrrolidin-3-ylmethyl]-acetamide (9.0 mg, 16%) as a white solid. [MH]⁺=488.0.

Example 4

2-[(4-Fluoro-benzenesulfonyl)-isopropyl-amino]-N-[1-(4-trifluoromethyl-phenyl)-pyrrolidin-3-ylmethyl]-acetamide

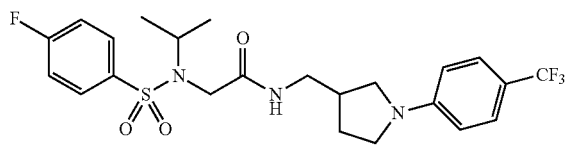 [SMILES: CC(C)N(CC(=O)NCC1CCN(c2ccc(C(F)(F)F)cc2)C1)S(=O)(=O)c1ccc(F)cc1]

A solution of crude [1-(4-trifluoromethyl-phenyl)-pyrrolidin-3-yl]-methylamine (26.6 mg, 0.11 mmol, crude) and [(4-fluoro-benzenesulfonyl)-isopropyl-amino]-acetic acid (30.0 mg, 0.11 mmol) in dichloromethane (5 mL) at 25° C. was treated with HATU (41.4 mg, 0.11 mmol). N,N-Diisopropylethylamine (28.2 mg, 0.22 mmol) was added to the solution. The reaction mixture was stirred for 2 h. The reaction mixture was then poured into 0.2 M aqueous KHSO₄ and extracted three times with ethyl acetate. The combined organic layers were washed three times with water and once with brine. The organic layer was then dried over magnesium sulfate, filtered and concentrated in vacuo. Flash column chromatography (50/50 hexanes/ethyl acetate) afforded 2-[(4-fluoro-benzenesulfonyl)-isopropyl-amino]-N-[1-(4-trifluoromethyl-phenyl)-pyrrolidin-3-ylmethyl]-acetamide (24.2 mg, 44%) as a white solid. [MH]⁺=502.1.

Example 5

2-[(4-Fluoro-benzenesulfonyl)-isopropyl-amino]-N—[(S)-1-(4-trifluoromethyl-phenyl)-piperidin-3-ylmethyl]-acetamide

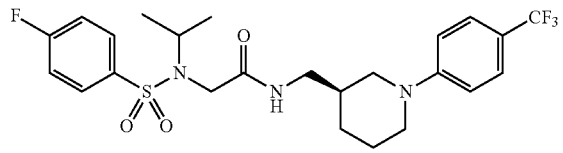 [SMILES: CC(C)N(CC(=O)NC[C@@H]1CCCN(c2ccc(C(F)(F)F)cc2)C1)S(=O)(=O)c1ccc(F)cc1]

This compound was obtained from the SFC separation of the corresponding racemate (from Example 2) using a chiral column (IA column from Chiral Technologies, 3×25 cm, methanol in carbon dioxide). The second fraction was concentrated and assigned as the (S)-isomer. [MH]⁺ 515.9.

Example 6

2-[(4-Fluoro-benzenesulfonyl)-isopropyl-amino]-N—[(R)-1-(4-trifluoromethyl-phenyl)-piperidin-3-ylmethyl]-acetamide

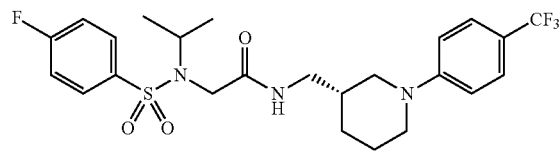

This compound was obtained from the SFC separation of the corresponding racemate (from Example 2) using a chiral column as described in Example 5. The first fraction was concentrated and assigned as the (R)-isomer. [MH]⁺ 515.9.

Example 7

2-[(4-Fluoro-benzenesulfonyl)-methyl-amino]-N-[(4-trifluoromethyl-phenyl)-morpholin-2-ylmethyl]-acetamide

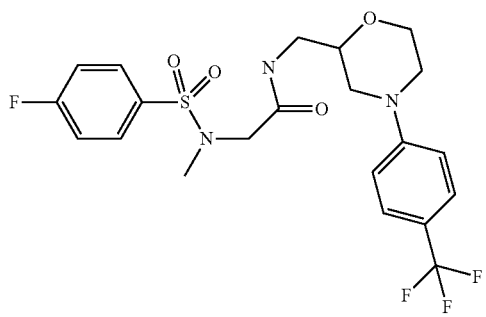 [SMILES: CN(CC(=O)NCC1CN(c2ccc(C(F)(F)F)cc2)CCO1)S(=O)(=O)c1ccc(F)cc1]

(4-(4-(Trifluoromethyl)phenyl)morpholin-2-yl)methylamine hydrochloride (99 mg, 0.34 mmol), 2-(4-fluoro-N-methylphenylsulfonamido)acetic acid (82.5 mg, 0.34 mmol), BOP reagent (148 mg, 0.34 mmol) and TEA (0.2 mL) were combined in 5 mL of dichloromethane. The mixture was stirred overnight and solvents were evaporated. The residue was extracted with ethyl acetate and water. The organic layer was washed with sodium bicarbonate solution and dried. Solvents were evaporated and the residue was purified by ISCO flash column chromatography (11 g silica gel, ethyl acetate in hexanes 0% to 80%) to give the desired compound as a white solid (140 mg, 86%). [MH]⁺=489.9.

Example 8

2-[(4-Fluoro-benzenesulfonyl)-isopropyl-amino]-N-[4-(4-trifluoromethyl-phenyl)-morpholin-2-ylmethyl]-acetamide

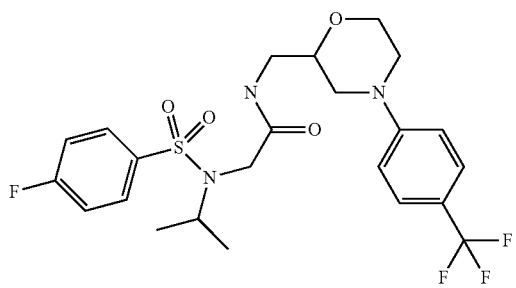 [SMILES: CC(C)N(CC(=O)NCC1CN(c2ccc(C(F)(F)F)cc2)CCO1)S(=O)(=O)c1ccc(F)cc1]

(4-(4-(Trifluoromethyl)phenyl)morpholin-2-yl)methylamine hydrochloride (99 mg, 0.34 mmol), 2-[(4-fluoro-benzenesulfonyl)-isopropyl-amino]-acetic acid (96 mg, 0.35 mmol), BOP reagent (154 mg, 0.35 mmol) and TEA (0.2 mL) were combined in 5 mL of dichloromethane. The mixture was stirred overnight and solvents were evaporated. The residue was extracted with ethyl acetate and water. The organic layer was washed with sodium bicarbonate solution and dried. Solvents were evaporated and the residue was purified by ISCO flash column chromatography (11 g silica gel, ethyl acetate in hexanes 0% to 50%) to give the desired compound as a white solid (133 mg, 74%). [MH]$^+$=517.9.

Example 9

2-[Ethyl-(4-fluoro-benzenesulfonyl)-amino]-N-[4-(4-trifluoromethyl-phenyl)-morpholin-2-ylmethyl]-acetamide

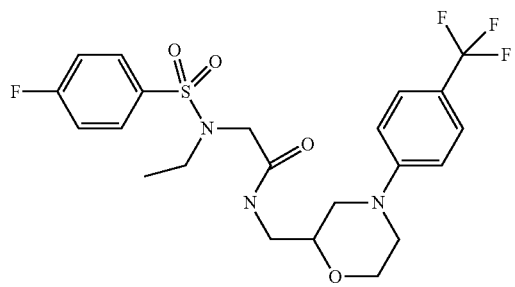 [SMILES: CCN(CC(=O)NCC1CN(c2ccc(C(F)(F)F)cc2)CCO1)S(=O)(=O)c1ccc(F)cc1]

(4-(4-(Trifluoromethyl)phenyl)morpholin-2-yl)methylamine hydrochloride (99 mg, 0.34 mmol), [ethyl-(4-fluoro-benzenesulfonyl)-amino]-acetic acid (87.2 mg, 0.34 mmol), BOP reagent (148 mg, 0.34 mmol) and TEA (0.2 mL) were combined in 5 mL of dichloromethane. The mixture was stirred overnight and solvents were evaporated. The residue was extracted with ethyl acetate and water. The organic layer was washed with sodium bicarbonate solution and dried. Solvents were evaporated and the residue was purified by ISCO flash column chromatography (11 g silica gel, ethyl acetate in hexanes 0% to 60%) to give the desired compound as a white solid (125 mg, 74%). [MH]$^+$=504.0.

Example 10

2-[(4-Fluoro-benzenesulfonyl)-isopropyl-amino]-N—[(R)-4-(4-trifluoromethyl-phenyl)-morpholin-2-ylmethyl]-acetamide

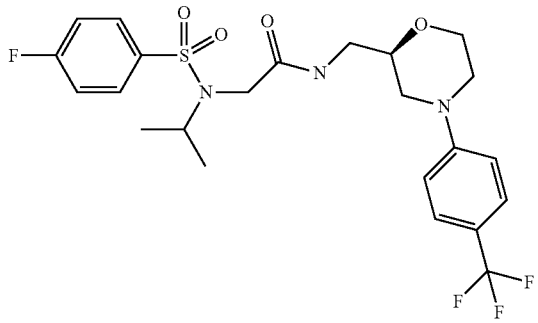 [SMILES: CC(C)N(CC(=O)NC[C@@H]1CN(c2ccc(C(F)(F)F)cc2)CCO1)S(=O)(=O)c1ccc(F)cc1]

This compound was obtained from the SFC separation of the corresponding racemate (from Example 8) using a chiral column (Diacel IA 3.0×25 cm, 40% methanol in $CO_2$). The first fraction was concentrated and assigned as the (R)-isomer. [MH]$^+$ 517.9.

Example 11

2-[(4-Fluoro-benzenesulfonyl)-isopropyl-amino]-N—[(S)-4-(4-trifluoromethyl-phenyl)-morpholin-2-ylmethyl]-acetamide

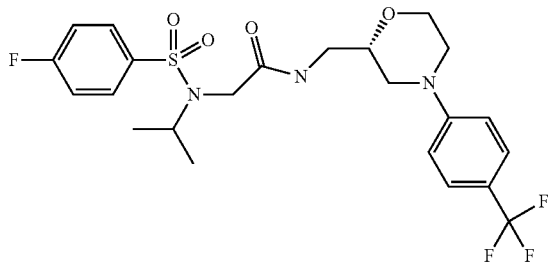 [SMILES: CC(C)N(CC(=O)NC[C@H]1CN(c2ccc(C(F)(F)F)cc2)CCO1)S(=O)(=O)c1ccc(F)cc1]

This compound was obtained from the SFC separation of the corresponding racemate (from Example 8) using a chiral column (Diacel IA 3.0×25 cm, 40% methanol in $CO_2$). The second fraction was concentrated and assigned as the (S)-isomer. [MH]$^+$ 517.9.

Example 12

2-[(4-Fluoro-benzenesulfonyl)-isopropyl-amino]-N-[4-(5-trifluoromethyl-pyridin-2-yl)-morpholin-2-ylmethyl]-acetamide

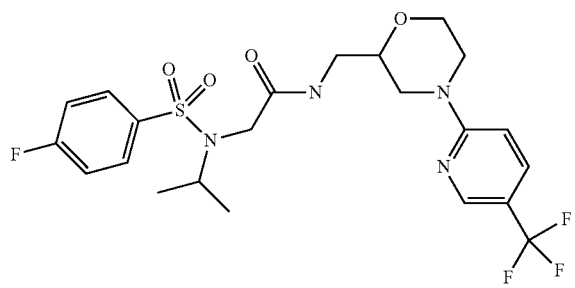 [SMILES: CC(C)N(CC(=O)NCC1CN(c2ccc(C(F)(F)F)cn2)CCO1)S(=O)(=O)c1ccc(F)cc1]

2-(4-Fluoro-N-isopropylphenylsulfonamido)acetic acid (108 mg, 0.39 mmol), (4-(5-(trifluoromethyl)pyridin-2-yl)morpholin-2-yl)methylamine dihydrochloride (131 mg, 0.39 mmol) and TEA (0.22 mL) were combined in dichloromethane (6 mL). To this stirred solution was added BOP reagent (174 mg, 0.39 mmol). The mixture was stirred at room temperature for 6 h. Solvents were evaporated and the residue was extracted with ethyl acetate and water, washed with sodium bicarbonate solution and dried. Solvents were evaporated. The residue was purified by ISCO flash column chromatography (0% to 100% ethyl acetate in hexanes) to give a white powder (160 mg, 79%). [MH]$^+$=519.0.

Example 13

IC$_{50}$ Determinations

Dose Response Assay: ChanTest hTRPA1-CHO Stably Transfected Cell Line
Cell Culture and Assay Reagents:

| | |
|---|---|
| Ham's F12 | (GIBCO #11765-047) |
| Tetracycline-free Fetal Bovine Serum | (ClonTech#631106, Lot A301097018) |

-continued

| | |
|---|---|
| Blasticidin (10 mg/ml stock) | (GIBCO #A11139-02) |
| Zeocin (100 mg/ml stock) | (GIBCO #R250-01) |
| Doxycycline | (SIGMA #D9891) |
| Penicillin-Spreptomycin solution (100X) | (GIBCO #15140-122) |
| GlutaMAX (100X) | (GIBCO #35050) |
| Trypsin-EDTA | (GIBCO #25200-056) |
| PBS (without Calcium and Magnesium) | (GIBCO #14190) |
| HBSS | (GIBCO #14025) |
| Hepes | (GIBCO #15630) |
| BSA (fatty acid free, low endotoxin) | (SIGMA #A8806-5G) |
| DMSO | (SIGMA #D2650) |
| AP-18 | (SIGMA #A7232) |
| Cinnamaldehyde | (SIGMA #W228613) |
| ATP | (SIGMA #A-6419) |
| 2-Aminoethyl diphenylborinate | (SIGMA #D9754) |
| Menthol | (Sigma #M2772) |
| FLIPR Calcium 3 Assay Kit | (Molecular Devices #R8108) |
| Probenecid | (INVITROGEN #36400) |
| Plates | (BD #35-3962) |

CHO-K1 Tet-on HOMSA TRPA1 Clone 20
Chinese Hamster Ovary cells, inducible expression
Clone #20, received at passage #26
Channel expression in this cell line has been shown to be stable for at least 80 passages
Verified Mycoplasma free with MycoAlert Kit
Cell line expanded and banked
Growth Conditions:
Growth Media for CHO-K1 Tet-on HOMSA TRPA1 Clone 20
Ham's F-12 with 10% tetracycline-free FBS
1× penicillin-streptomycin
1× glutamax
0.01 mg/ml Blasticidin
0.40 mg/ml Zeocin
The cell line doubling rate was ~15 hours. The culture plates did not exceed 80% confluency.
To induce expression, tetracycline was added to blasticidin/zeocin-free media at a final concentration of 1 ug/ml. Experiments were run at 24 hours post induction.
Plating Conditions CHOK1/TRPA1 Cells:
Harvested cells with 0.025% trypsin/EDTA.
Resuspended cells in growth media without selection antibiotics.
Measured cell density and diluted to $2.4 \times 10^5$ cells/ml in media containing 1 ug/ml Doxycycline Plate 25 ul/well into 384 well black/clear tissue culture-treated plates.
Incubated overnight at 37° C.
Calcium Flux Assay:
Day of Assay:
Reagents:
Replacement Buffer: Hank's Balanced Salt Solution, 20 mM HEPES along with 0.005% BSA and 2× Probenecid
Dye Loading Buffer: Cal-3 NW Calcium dye was prepared by dissolving the contents of one vial with 500 ml Hank's Balanced Salt Solution containing 20 mM HEPES.
Control Compounds for CHOK1/TRPA1 Cells:
AP-18, stock 10 mM, prepare 3.5× compound dilution in a Compound Buffer (HBSS/20 mM HEPES/0.005% BSA)—final concentration 10 uM.
Preparation of Cinnamaldehyde (Agonist Addition):
FW=132.16
Specific gravity=1.046 gm/cc
1.32 gm/1.046 gm/cc=1.26 ml of stock
Add 1.74 ml DMSO=3.3 M stock
Working solution 4.5× (final 100 uM in Compound Buffer: HBSS/20 mM HEPES/0.005% BSA)

Compounds dilutions were prepared from 5 or 10 mM stock (100% DMSO):

Adjustments of volumes and concentrations were made at time of titration to reflect desired final assay concentrations.

Compounds were tested at either 20 µM three folds dilution 11 steps out or 30 µM two folds dilution 11 steps out.

3 µl of diluted compound were transferred into Weidmann 384-well plate in duplicates side-by-side.

Compound plates were resuspended with 100 ul of HBSS/20 mM HEPES/0.005% BSA buffer (Compound Buffer):

column 1A-H: buffer/DMSO (bk)

column 2A-H: AP-18 (control antagonist for CHOK1 TRPA1 cells)

column 1I-P: ATP (control for CHOK1 teton cells)

column 2 I-P: 2APB (control antagonist for CHOK1/TRPM8 cells).

Growth media was removed from the cell plates (20 ul) and 20 ul of the Replacement Buffer was added followed by addition of 25 ul of diluted dye. All three steps were performed using a Plate Washer BioTek 407. The plates were then incubated for 30' at RT.

After incubation, both the cell and compound plates were brought to the FLIPR and 20 ul of the diluted compounds/antagonist/bk were transferred to the cell plates by the FLIPR. Plates were then incubated for 30' at room temperature. After 30' incubation, plates were returned to the FLIPR and 20 ul of 4.5× Cinnamaldehyde was added to the cell plates. During the compound addition as well as agonist addition, fluorescence readings were taken simultaneously from all 384 wells of the cell plate every 1.5 seconds. Five readings were taken to establish a stable baseline, then 20 ul of sample was rapidly (30 ul/sec) and simultaneously added to each well of the cell plate. The fluorescence was continuously monitored before, during and after sample/agonist addition for a total elapsed time of 100 seconds (compound addition) and 120 seconds (agonist addition). Responses (increase in peak fluorescence) in each well following agonist addition was determined. The initial fluorescence reading from each well, prior to ligand stimulation, was used a zero baseline value for the data from that well. The responses were expressed as % inhibition of the inhibitor control as shown in Table 1 below:

TABLE 1

| Example | h-TRPA1 $IC_{50}$ (µM) |
|---|---|
| 1 | 0.494 |
| 2 | 0.233 |
| 3 | 0.634 |
| 4 | 0.425 |
| 5 | 0.307 |
| 6 | 0.504 |
| 7 | 1.516 |
| 8 | 0.193 |
| 9 | 0.226 |
| 10 | 1.31 |
| 11 | 0.151 |
| 12 | 0.385 |

It is to be understood that the invention is not limited to the particular embodiments of the invention described above, as variations of the particular embodiments may be made and still fall within the scope of the appended claims.

The invention claimed is:
1. A compound of formula (I)

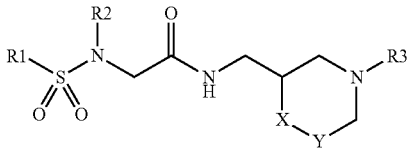

wherein:
X is —CH₂— or oxygen;
Y is —(CH₂)$_n$—;
R1 is phenyl optionally substituted with halogen;
R2 is lower alkyl;
R3 is trifluoromethyl-phenyl, trifluoromethyl-pyridinyl, trifluoromethyl-pyridazinyl, trifluoromethyl-pyrimidinyl or trifluoromethyl-pyrazinyl; and
n is 0 or 1, provided that n is not 0 when X is oxygen;
or a pharmaceutically acceptable salt thereof.
2. A compound according to claim 1, wherein X is —CH₂—.
3. A compound according to claim 1, wherein X is oxygen.
4. A compound according to claim 1, wherein n is 0.
5. A compound according to claim 1, wherein n is 1.
6. A compound according to claim 1, wherein R1 is halophenyl.
7. A compound according to claim 1, wherein R1 is fluorophenyl.
8. A compound according to claim 1, wherein R2 is methyl, ethyl, isopropyl or tert-butyl.
9. A compound according to claim 1, wherein R2 is methyl, ethyl or isopropyl.
10. A compound according to claim 1, wherein R3 is trifluoromethyl-phenyl or trifluoromethyl-pyridinyl.
11. A compound according to claim 1, wherein, wherein R3 is trifluoromethyl-phenyl.
12. A compound according to claim 1, wherein R3 is trifluoromethyl-pyridinyl.
13. A compound according to claim 1, wherein the compound is selected from the group consisting of:
2-[Ethyl-(4-fluoro-benzenesulfonyl)-amino]-N-[1-(4-trifluoromethyl-phenyl)-piperidin-3-ylmethyl]-acetamide;
2-[(4-Fluoro-benzenesulfonyl)-isopropyl-amino]-N-[1-(4-trifluoromethyl-phenyl)-piperidin-3-ylmethyl]-acetamide;
2-[Ethyl-(4-fluoro-benzenesulfonyl)-amino]-N-[1-(4-trifluoromethyl-phenyl)-pyrrolidin-3-ylmethyl]-acetamide;
2-[(4-Fluoro-benzenesulfonyl)-isopropyl-amino]-N-[1-(4-trifluoromethyl-phenyl)-pyrrolidin-3-ylmethyl]-acetamide;
2-[(4-Fluoro-benzenesulfonyl)-isopropyl-amino]-N-[(S)-1-(4-trifluoromethyl-phenyl)-piperidin-3-ylmethyl]-acetamide;
2-[(4-Fluoro-benzenesulfonyl)-isopropyl-amino]-N-[(R)-1-(4-trifluoromethyl-phenyl)-piperidin-3-ylmethyl]-acetamide;
2-[(4-Fluoro-benzenesulfonyl)-methyl-amino]-N-[4-(4-trifluoromethyl-phenyl)-morpholin-2-ylmethyl]-acetamide;
2-[(4-Fluoro-benzenesulfonyl)-isopropyl-amino]-N-[4-(4-trifluoromethyl-phenyl)-morpholin-2-ylmethyl]-acetamide;
2-[Ethyl-(4-fluoro-benzenesulfonyl)-amino]-N-[4-(4-trifluoromethyl-phenyl)-morpholin-2-ylmethyl]-acetamide;
2-[(4-Fluoro-benzenesulfonyl)-isopropyl-amino]-N-[(R)-4-(4-trifluoromethyl-phenyl)-morpholin-2-ylmethyl]-acetamide;
2-[(4-Fluoro-benzenesulfonyl)-isopropyl-amino]-N-[(S)-4-(4-trifluoromethyl-phenyl)-morpholin-2-ylmethyl]-acetamide; and
2-[(4-Fluoro-benzenesulfonyl)-isopropyl-amino]-N-[4-(5-trifluoromethyl-pyridin-2-yl)-morpholin-2-ylmethyl]-acetamide.
14. A process for the manufacture of a compound of formula (I) comprising the reaction of a compound of formula (A)

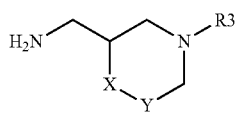

in the presence of a compound of formula (B)

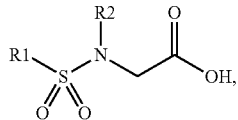

a coupling agent and a base, wherein R1 to R3 are as defined in claim 1.
15. A compound according to claim 1 when manufactured by the process of claim 14.
16. A pharmaceutical composition comprising a therapeutically effective amount of a compound according to claim 1 and a pharmaceutically acceptable carrier.
17. A method for the treatment of a respiratory disorder, the method comprising administering a therapeutically effective amount of a compound according to claim 1 to a subject in need thereof.
18. The method of claim 17, wherein the respiratory disorder is selected from the group consisting of chronic obstructive pulmonary disorder (COPD), asthma, allergic rhinitis and bronchospasm.

* * * * *